US008163031B2

(12) United States Patent
Truckai et al.

(10) Patent No.: US 8,163,031 B2
(45) Date of Patent: Apr. 24, 2012

(54) COMPOSITES AND METHODS FOR TREATING BONE

(75) Inventors: Csaba Truckai, Saratoga, CA (US); John H. Shadduck, Menlo Park, CA (US)

(73) Assignee: DFINE, Inc., San Jose, CA (US)

( * ) Notice: Subject to any disclaimer, the term of this patent is extended or adjusted under 35 U.S.C. 154(b) by 0 days.

(21) Appl. No.: 12/942,936

(22) Filed: Nov. 9, 2010

(65) Prior Publication Data

US 2011/0054482 A1    Mar. 3, 2011

Related U.S. Application Data

(63) Continuation of application No. 11/148,973, filed on Jun. 9, 2005, now abandoned.

(60) Provisional application No. 60/578,182, filed on Jun. 9, 2004.

(51) Int. Cl.
*A61F 2/28*    (2006.01)

(52) U.S. Cl. .................................. 623/23.51; 623/23.73

(58) Field of Classification Search .................... 606/94, 606/90–93, 99; 623/23.58–23.62, 23.19, 623/23.26, 23.48, 23.5, 23.51, 23.55, 23, 623/72, 23.73
See application file for complete search history.

(56) References Cited

U.S. PATENT DOCUMENTS

| | | | |
|---|---|---|---|
| 3,349,840 A | 10/1967 | Tope et al. | |
| 4,250,887 A | 2/1981 | Dardik et al. | |
| 4,265,618 A | 5/1981 | Herskovitz et al. | |
| 4,280,233 A | 7/1981 | Raab | |
| 4,294,251 A | 10/1981 | Greenwald et al. | |
| 4,338,925 A | 7/1982 | Miller | |
| 4,377,168 A | 3/1983 | Rzasa et al. | |
| 4,735,625 A | 4/1988 | Davidson | |
| 4,772,287 A | 9/1988 | Ray et al. | |
| 4,849,223 A | 7/1989 | Pratt et al. | |
| 4,959,104 A | 9/1990 | Iino et al. | |
| 4,963,151 A | 10/1990 | Ducheyne et al. | |
| 4,969,888 A | 11/1990 | Scholten et al. | |
| 4,969,906 A | 11/1990 | Kronman | |
| 5,037,437 A | 8/1991 | Matsen | |
| 5,051,482 A | 9/1991 | Tepic | |

(Continued)

FOREIGN PATENT DOCUMENTS

WO    WO 02/058592    8/2002

(Continued)

OTHER PUBLICATIONS

Carrodeguas, et al., "Injectable Acrylic Bone Cements for Vertebroplasty with Improved Properties", Journal of Biomedical Materials Research, XP002312783, vol. 68, No. 1, Jan. 15, 2004, pp. 94-104.

(Continued)

*Primary Examiner* — David Isabella
*Assistant Examiner* — Suba Ganesan
(74) *Attorney, Agent, or Firm* — Knobbe Martens Olson & Bear LLP

(57) ABSTRACT

A system and method for treating bone abnormalities including vertebral compression fractures and the like. In one method, an elastomeric composite implant body is inserted into bone. A rigid insert can be inserted into the elastomeric composite implant body. The elastomeric composite implant body can be deformed with the rigid insert to thereby form an interference fit between the bone and the implant.

12 Claims, 8 Drawing Sheets

U.S. PATENT DOCUMENTS

| | | | |
|---|---|---|---|
| 5,108,404 A | 4/1992 | Scholten et al. |
| 5,130,950 A | 7/1992 | Orban et al. |
| 5,145,250 A | 9/1992 | Planck et al. |
| 5,292,362 A | 3/1994 | Bass et al. |
| 5,334,626 A | 8/1994 | Lin |
| 5,360,450 A | 11/1994 | Giannini |
| 5,431,654 A | 7/1995 | Nic |
| 5,514,135 A | 5/1996 | Earle |
| 5,542,928 A | 8/1996 | Evans et al. |
| 5,571,189 A | 11/1996 | Kuslich |
| 5,574,075 A | 11/1996 | Draenert |
| 5,648,097 A | 7/1997 | Nuwayser |
| 5,665,122 A | 9/1997 | Kambin |
| 5,676,700 A | 10/1997 | Black et al. |
| 5,679,299 A | 10/1997 | Gilbert et al. |
| 5,693,099 A | 12/1997 | Harle |
| 5,769,880 A | 6/1998 | Truckai et al. |
| 5,788,711 A | 8/1998 | Lehner et al. |
| 5,814,681 A | 9/1998 | Hino et al. |
| 5,954,716 A | 9/1999 | Sharkey et al. |
| 5,961,554 A | 10/1999 | Janson et al. |
| 5,997,580 A | 12/1999 | Mastrorio et al. |
| 6,048,346 A | 4/2000 | Reiley et al. |
| 6,075,067 A | 6/2000 | Lidgren |
| 6,122,549 A | 9/2000 | Sharkey et al. |
| 6,129,763 A | 10/2000 | Chauvin et al. |
| 6,143,036 A | 11/2000 | Comfort |
| 6,171,312 B1 | 1/2001 | Beaty |
| 6,231,615 B1 | 5/2001 | Preissman |
| 6,235,043 B1 | 5/2001 | Reiley et al. |
| 6,236,020 B1 | 5/2001 | Friedman |
| 6,248,110 B1 | 6/2001 | Reiley et al. |
| 6,261,289 B1 | 7/2001 | Levy |
| 6,264,659 B1 | 7/2001 | Ross et al. |
| 6,280,456 B1 | 8/2001 | Scribner et al. |
| 6,309,420 B1 | 10/2001 | Preissman |
| 6,312,254 B1 | 11/2001 | Friedman |
| 6,316,885 B1 | 11/2001 | Collins et al. |
| 6,319,255 B1 | 11/2001 | Grundei et al. |
| 6,332,894 B1 | 12/2001 | Stalcup et al. |
| 6,348,679 B1 | 2/2002 | Ryan et al. |
| 6,358,254 B1 | 3/2002 | Anderson |
| 6,375,659 B1 | 4/2002 | Erbe et al. |
| 6,395,007 B1 | 5/2002 | Bhatnagar et al. |
| 6,419,704 B1 | 7/2002 | Ferree |
| 6,425,919 B1 | 7/2002 | Lambrecht |
| 6,425,923 B1 | 7/2002 | Stalcup et al. |
| 6,439,439 B1 | 8/2002 | Rickard |
| 6,443,988 B2 | 9/2002 | Felt et al. |
| 6,447,514 B1 | 9/2002 | Stalcup et al. |
| 6,458,127 B1 | 10/2002 | Truckai et al. |
| 6,458,375 B1 | 10/2002 | Gertzman et al. |
| 6,485,436 B1 | 11/2002 | Truckai |
| 6,524,102 B2 | 2/2003 | Davis |
| 6,558,428 B2 | 5/2003 | Park |
| 6,607,557 B1 | 8/2003 | Brosnahan et al. |
| 6,610,079 B1 | 8/2003 | Li et al. |
| 6,613,054 B2 | 9/2003 | Scribner et al. |
| 6,620,185 B1 | 9/2003 | Harvie et al. |
| 6,632,235 B2 | 10/2003 | Weikel et al. |
| 6,649,888 B2 | 11/2003 | Ryan et al. |
| 6,676,664 B1 | 1/2004 | Al-Assir |
| 6,706,069 B2 | 3/2004 | Berger |
| 6,709,149 B1 | 3/2004 | Tepic |
| 6,712,852 B1 | 3/2004 | Chung et al. |
| 6,719,773 B1 | 4/2004 | Boucher et al. |
| 6,723,095 B2 | 4/2004 | Hammerslag |
| 6,726,691 B2 | 4/2004 | Osorio et al. |
| 6,736,537 B2 | 5/2004 | Coffeen et al. |
| 6,740,093 B2 | 5/2004 | Hochschuler et al. |
| 6,753,358 B2 | 6/2004 | Fischer et al. |
| 6,767,936 B2 | 7/2004 | Walz et al. |
| 6,790,233 B2 | 9/2004 | Brodke et al. |
| 6,814,736 B2 | 11/2004 | Reiley et al. |
| 6,832,988 B2 | 12/2004 | Sproul |
| 6,835,206 B2 | 12/2004 | Jackson |
| 6,872,403 B2 | 3/2005 | Pienkowski et al. |
| 6,899,713 B2 | 5/2005 | Shaolian et al. |
| 6,955,691 B2 | 10/2005 | Chae et al. |
| 6,958,061 B2 | 10/2005 | Truckai et al. |
| 6,964,667 B2 | 11/2005 | Shaolian et al. |
| 6,979,341 B2 | 12/2005 | Scribner et al. |
| 6,979,352 B2 | 12/2005 | Reynolds |
| 6,985,061 B2 | 1/2006 | Hafskjold et al. |
| 7,008,433 B2 | 3/2006 | Voellmicke et al. |
| 7,014,658 B2 | 3/2006 | Ralph et al. |
| 7,044,954 B2 | 5/2006 | Reiley et al. |
| 7,081,125 B2 | 7/2006 | Edwards et al. |
| 7,108,696 B2 | 9/2006 | Daniel et al. |
| 7,112,201 B2 | 9/2006 | Truckai et al. |
| 7,153,307 B2 | 12/2006 | Scribner et al. |
| 7,166,121 B2 | 1/2007 | Reiley et al. |
| 7,186,267 B2 | 3/2007 | Aston et al. |
| 7,189,263 B2 | 3/2007 | Erbe et al. |
| 7,191,285 B2 | 3/2007 | Scales |
| 7,226,481 B2 | 6/2007 | Kuslich |
| 7,241,303 B2 | 7/2007 | Reiss et al. |
| 7,252,672 B2 | 8/2007 | Yetkinler |
| 7,258,700 B2 | 8/2007 | Lambrecht et al. |
| 7,259,210 B2 * | 8/2007 | Puckett et al. ............ 623/23.62 |
| 7,261,720 B2 | 8/2007 | Stevens et al. |
| 7,273,523 B2 | 9/2007 | Wenz |
| 7,306,598 B2 | 12/2007 | Truckai et al. |
| 7,318,823 B2 | 1/2008 | Sharps et al. |
| 7,357,798 B2 | 4/2008 | Sharps et al. |
| 7,399,739 B2 | 7/2008 | Shimp |
| 7,431,763 B2 | 10/2008 | Zimmermann |
| 7,435,247 B2 | 10/2008 | Woloszko et al. |
| 7,510,579 B2 | 3/2009 | Preissman |
| 7,559,932 B2 | 7/2009 | Truckai et al. |
| 7,662,133 B2 | 2/2010 | Scarborough et al. |
| 7,678,116 B2 | 3/2010 | Truckai et al. |
| 7,708,733 B2 | 5/2010 | Sanders et al. |
| 7,717,918 B2 | 5/2010 | Truckai et al. |
| 7,722,620 B2 | 5/2010 | Truckai et al. |
| 7,722,624 B2 | 5/2010 | Boucher et al. |
| 2002/0026195 A1 | 2/2002 | Layne et al. |
| 2002/0068974 A1 | 6/2002 | Kuslich et al. |
| 2002/0127720 A1 * | 9/2002 | Erbe et al. ................ 435/395 |
| 2002/0147497 A1 | 10/2002 | Belef et al. |
| 2003/0032929 A1 | 2/2003 | McGuckin |
| 2003/0130738 A1 | 7/2003 | Hovda et al. |
| 2003/0220648 A1 | 11/2003 | Osorio et al. |
| 2003/0233096 A1 | 12/2003 | Osorio et al. |
| 2004/0024410 A1 | 2/2004 | Olson, Jr. et al. |
| 2004/0083002 A1 | 4/2004 | Belef et al. |
| 2004/0138748 A1 | 7/2004 | Boyer, II et al. |
| 2004/0172132 A1 | 9/2004 | Ginn |
| 2004/0193171 A1 | 9/2004 | DiMauro et al. |
| 2004/0228898 A1 | 11/2004 | Ross et al. |
| 2004/0267272 A1 | 12/2004 | Henniges |
| 2005/0010231 A1 | 1/2005 | Myers |
| 2005/0015148 A1 | 1/2005 | Jansen et al. |
| 2005/0043816 A1 * | 2/2005 | Datta et al. ............... 623/23.61 |
| 2005/0113843 A1 | 5/2005 | Arramon |
| 2005/0180806 A1 | 8/2005 | Green et al. |
| 2005/0209595 A1 | 9/2005 | Karmon |
| 2005/0222681 A1 | 10/2005 | Richley et al. |
| 2005/0245938 A1 | 11/2005 | Kochan |
| 2006/0052743 A1 | 3/2006 | Reynolds |
| 2006/0052794 A1 | 3/2006 | McGill et al. |
| 2006/0074433 A1 | 4/2006 | McGill et al. |
| 2006/0079905 A1 | 4/2006 | Beyar et al. |
| 2006/0100635 A1 | 5/2006 | Reiley et al. |
| 2006/0150862 A1 | 7/2006 | Zhao et al. |
| 2006/0198865 A1 | 9/2006 | Freyman et al. |
| 2006/0229628 A1 | 10/2006 | Truckai et al. |
| 2006/0264965 A1 | 11/2006 | Shadduck et al. |
| 2007/0027230 A1 | 2/2007 | Beyar et al. |
| 2007/0112299 A1 | 5/2007 | Smit et al. |
| 2007/0118144 A1 | 5/2007 | Truckai et al. |
| 2007/0162043 A1 | 7/2007 | Truckai et al. |
| 2007/0185231 A1 | 8/2007 | Liu et al. |
| 2007/0191858 A1 | 8/2007 | Truckai et al. |
| 2007/0191964 A1 | 8/2007 | Preissman |
| 2007/0233148 A1 | 10/2007 | Truckai et al. |

| | | |
|---|---|---|
| 2008/0103505 A1 | 5/2008 | Fransen |
| 2008/0195112 A1 | 8/2008 | Liu et al. |
| 2009/0024161 A1 | 1/2009 | Bonutti et al. |

FOREIGN PATENT DOCUMENTS

| | | |
|---|---|---|
| WO | WO 02/064062 | 8/2002 |
| WO | WO 02/087416 | 11/2002 |
| WO | WO 2004/075954 | 9/2004 |
| WO | WO 2006/031490 | 3/2006 |
| WO | WO 2006/062916 | 6/2006 |
| WO | WO 2006/130491 | 12/2006 |
| WO | WO 2007/028120 | 3/2007 |
| WO | WO 2008/097855 | 8/2008 |
| WO | WO 2009/108893 | 9/2009 |

OTHER PUBLICATIONS

Exam Report for EPO App. 05 848 386.8 dated Sep. 18, 2009 in 5 pgs.

Furderer S, Anders M, Schwindling B, Salick M, Duber C, Wenda K, Urban R, Gluck M, Eysel P., "Vertebral body stenting. A method for repositioning and augmenting vertebral compression fractures", Orthopade. Apr. 2002; 31(4):356-61, Abstract.

International Search Report, mailing date Apr. 16, 2007, PCT/US2006/034409.

International Search Report, mailing date May 31, 2006, PCT/US2005/044055, 4 pg.

International Search Report, mailing date Jun. 20, 2006, PCT/US2005/043984, 3 pg.

B. Heublein, R. Rohde, V. Kaese, M. Niemeyer, W. Hartung, A. Haverich, "Biocorrosion of magnesium alloys: a new principle in cardiovascular implant technology?", *Heart*, 2003; 89:651-656.

* cited by examiner

COMPOSITES AND METHODS FOR TREATING BONE

CROSS-REFERENCE TO RELATED APPLICATIONS

This application is a continuation of U.S. application Ser. No. 11/148,973 filed Jun. 9, 2005, which claims benefit of Provisional U.S. Patent Application No. 60/578,182 filed Jun. 9, 2004, titled Scaffold Composites and Methods for Treating Abnormalities in Bone, the entire contents of all of which are hereby incorporated by reference in their entirety and should be considered a part of this specification.

BACKGROUND OF THE INVENTION

1. Field of the Invention

This invention relates to bone implant materials and methods and more particularly to composite materials including an elastomer component for treating abnormalities in bones such as compression fractures of vertebra, necrosis of femurs, joint implants and the like. An exemplary method includes introducing a flowable composite material into the interior of a bone wherein increasing pressures result in the elastomer component causing a differential apparent viscosity within selected regions across the flowable material to thereby allow controlled application of forces to the bone for reducing a fracture.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion: The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the affected population will grow steadily as life expectancy increases. Osteoporosis affects the entire skeleton but most commonly causes fractures in the spine and hip. Spinal or vertebral fractures also have serious consequences, with patients suffering from loss of height, deformity and persistent pain which can significantly impair mobility and quality of life. Fracture pain usually lasts 4 to 6 weeks, with intense pain at the fracture site. Chronic pain often occurs when one level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporotic bone, the sponge-like cancellous bone has pores or voids that increase in dimension, making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. In one percutaneous vertebroplasty technique, bone cement such as PMMA (polymethylmethacrylate) is percutaneously injected into a fractured vertebral body via a trocar and cannula system. The targeted vertebrae are identified under fluoroscopy. A needle is introduced into the vertebral body under fluoroscopic control to allow direct visualization. A transpedicular (through the pedicle of the vertebrae) approach is typically bilateral but can be done unilaterally. The bilateral transpedicular approach is typically used because inadequate PMMA infill is achieved with a unilateral approach.

In a bilateral approach, approximately 1 to 4 ml of PMMA are injected on each side of the vertebra. Since the PMMA needs to be forced into cancellous bone, the technique requires high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasasion are critical to the technique—and the physician terminates PMMA injection when leakage is evident. The cement is injected using small syringe-like injectors to allow the physician to manually control the injection pressures.

Kyphoplasty is a modification of percutaneous vertebroplasty. Kyphoplasty involves a preliminary step that comprises the percutaneous placement of an inflatable balloon tamp in the vertebral body. Inflation of the balloon creates a cavity in the bone prior to cement injection. Further, the proponents of percutaneous kyphoplasty have suggested that high pressure balloon-tamp inflation can at least partially restore vertebral body height. In kyphoplasty, it has been proposed that PMMA can be injected at lower pressures into the collapsed vertebra since a cavity exists to receive the cement—which is not the case in conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles, Leakage of PMMA during vertebroplasty can result in very serious complications including compression of adjacent structures that necessitate emergency decompressive surgery.

Leakage or extravasasion of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al., "The Analysis of Polymethylmethacrylate Leakage after Vertebroplasty for Vertebral Body Compression Fractures", Jour. of Korean Neurosurg. Soc. Vol. 35, No. 5 (May 2004) pp. 478-82, (http://www.jkns.or.kr/htm/abstract.asp?no=042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al., "Asymptomatic diffuse pulmonary embolism caused by acrylic cement: an unusual complication of percutaneous vertebroplasty", Ann. Rheum. Dis. 2003; 62:85-86. The vapors from PMMA preparation and injection are also cause for concern. See Kirby. B., et al., "Acute bronchospasm due to exposure to polymethlmethacrylate vapors during percutaneous vertebroplasty", Am. J. Roentgenol. 2003; 180:543-544.

Another disadvantage of PMMA is its inability to undergo remodeling—and the inability to use the PMMA to deliver osteoinductive agents, growth factors, chemotherapeutic agent and the like. Yet another disadvantage of PMMA is the need to add radiopaque agents which lower its viscosity with unclear consequences on its long-term endurance.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance with the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which first crushes and compacts cancellous bone. Expansion of the balloon under high pressures close to cortical bone can fracture the cortical bone, or cause regional damage to the cortical bone that can result in cortical bone necrosis. Such cortical bone damage is highly undesirable and results in weakened cortical endplates.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide systems and methods for use in treatment of vertebral compression fractures that provide a greater degree of control over introduction of bone support material, and that provide better outcomes. Embodiments of the present invention meet one or more of the above needs, or other needs, and provide several other advantages in a novel and non-obvious manner.

SUMMARY OF THE INVENTION

The invention provides systems and method of treating bone abnormalities including vertebral compression fractures, bone tumors and cysts, avascular necrosis of the femoral head and the like. In one embodiment, an elastomeric composite implant body is inserted into bone. A rigid insert can be inserted into the elastomeric composite implant body. The elastomeric composite implant body can be deformed with the rigid insert to thereby form an interference fit between the bone and the implant.

A method according to some embodiments can include inserting an elastomeric composite implant body having a predetermined shape into an opening in a bone, the composite implant body defining an internal bore along a longitudinal axis of the composite implant body. The elastomeric composite implant body can include at least one first region and at least one second region. Each region can comprise an elastomeric polymer and reticulated elements dispersed within the elastomeric polymer. The at least one first region can have a different elastic modulus from the at least one second region, the difference being a function of differences between the reticulated elements in the at least one first region as compared to the reticulated elements in the at least one second region. The method can further include inserting a rigid insert into the bore in the elastomeric composite implant body to secure the implant in the bone and deforming the elastomeric composite implant body with the rigid insert to thereby form an interference fit between the bone and the implant, the at least one first region deforming in a manner different from the at least one second region.

BRIEF DESCRIPTION OF THE DRAWINGS

In the following detailed description, similar reference numerals are used to depict like elements in the various figures.

FIG. 3B illustrate the elastomeric material of FIG. 3A being inserted in the bore in the bone.

DETAILED DESCRIPTION OF THE PREFERRED EMBODIMENT

Figure 1A:
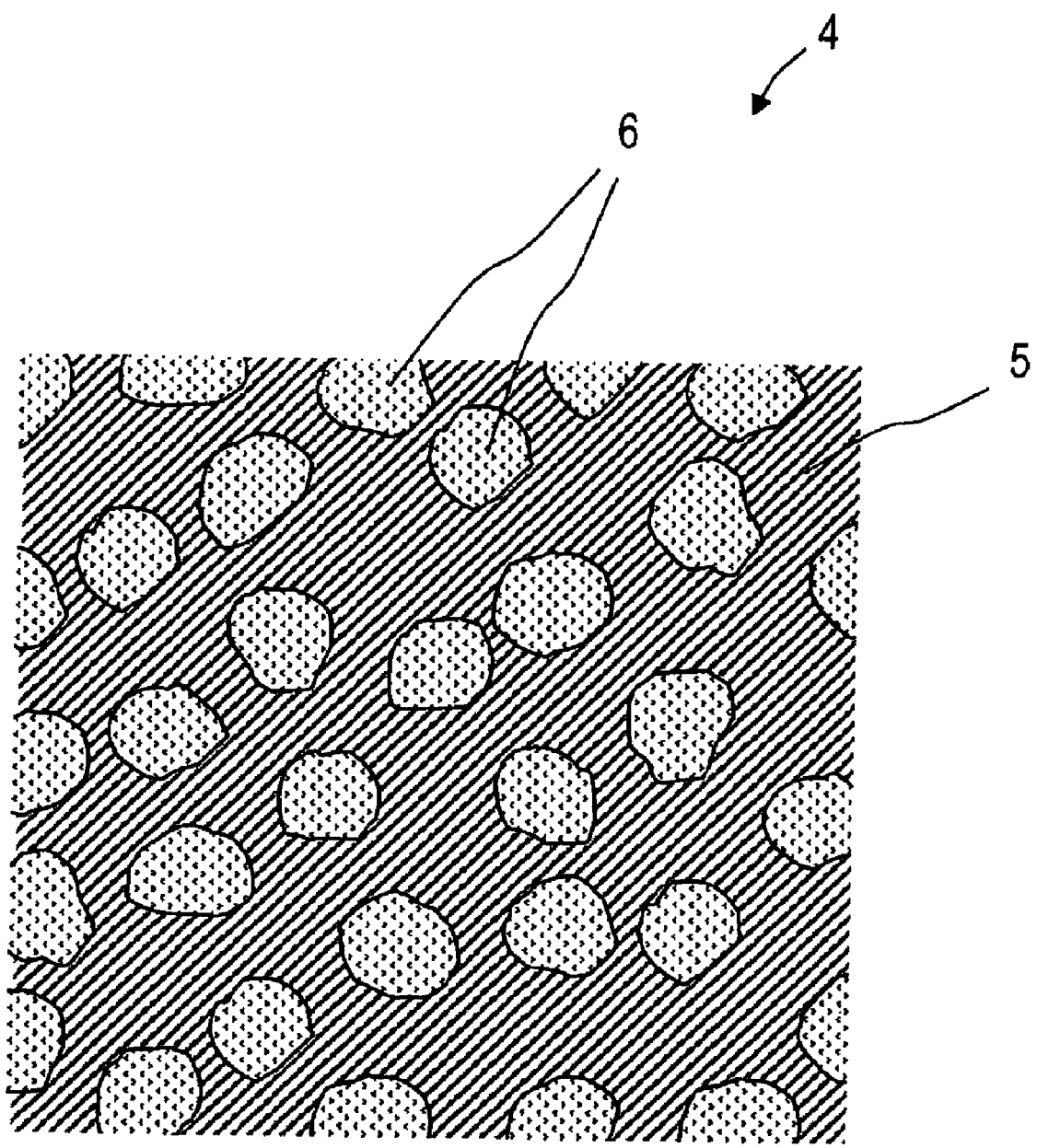
FIG. 1A is a greatly enlarged sectional view of a flowable composite bone infill material such as PMMA with a volume of elastomeric elements or particles carried therein.to FIG. 1B is a greatly enlarged sectional view of an elastomeric element of FIG. 1A with reticulated elements dispersed within the elastomer.
Figure 1B:
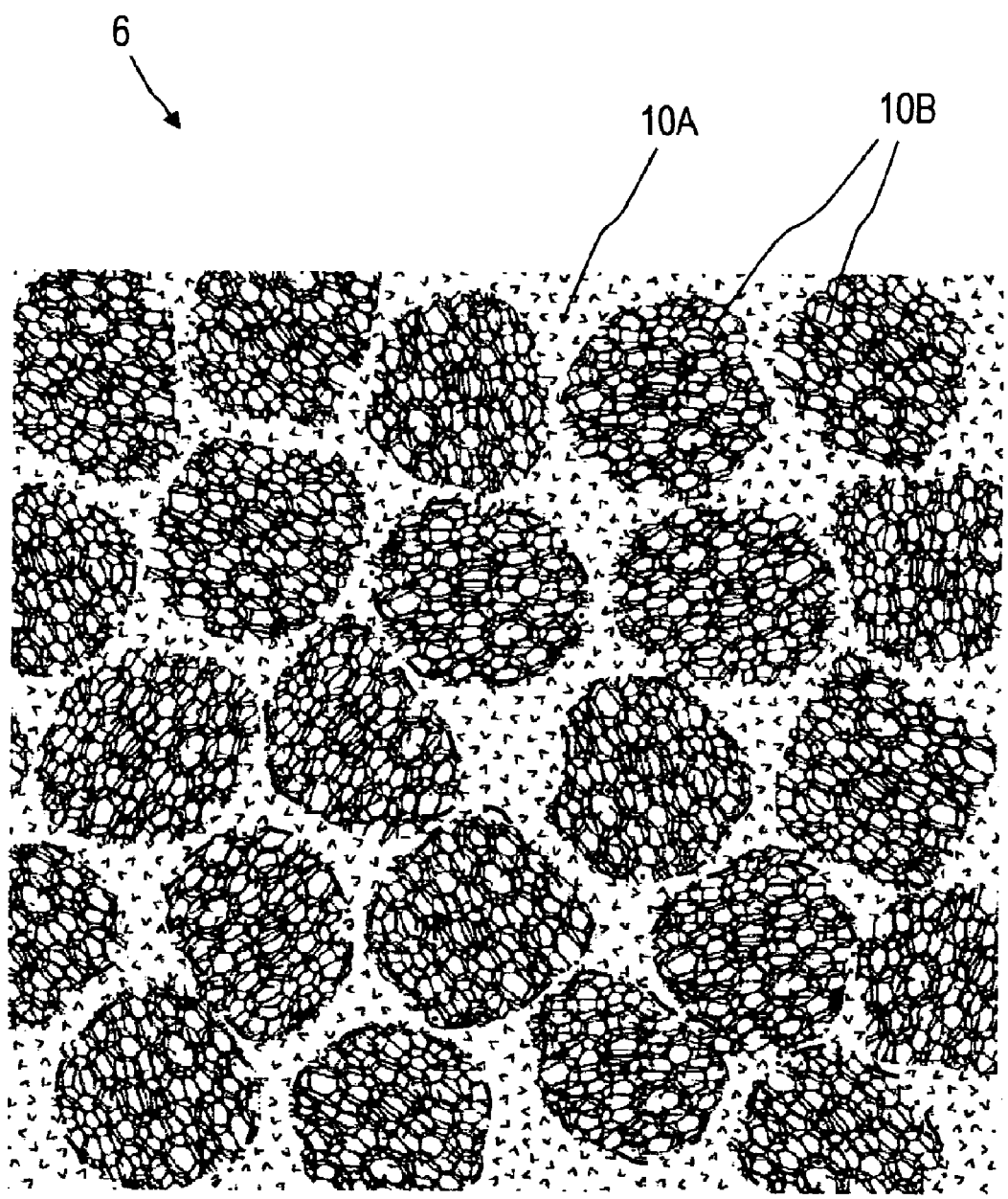

FIG. 1A illustrates a cross-sectional view of fill material 4 that comprises flowable component 5 with elastomeric polymer component 6 dispersed therein. The flowable component or material 5 is an in-situ hardenable bone cement (e.g., PMMA) that is intermixed with elastomeric component 6 that comprises a plurality of small elastomeric elements, such as silicone particles or elements of another biocompatible polymer. The flowable material 5 and elastomeric elements 6 can be intermixed prior to introduction into bone or contemporaneous with introduction into bone from separate channels in an introducer. The elastomeric elements 6 are typically dimensioned to be small enough to allow their passage within the openings of cancellous bone in a targeted treatment site. In one embodiment as depicted in FIG. 1B, the elastomeric elements 6 themselves comprise a composite of base elastomer 10A and reticulated, open-cell scaffold structures indicated at 10B. Such reticulated open-cell structures can allow for later bone ingrowth into the surface of the volume of fill material. The term "reticulated" as used herein describes open-cell structures 10B and means having the appearance of, or functioning as, a wire-like network or a substantially rigid net-like structure. The terms reticulated and trabecular are used interchangeably herein to describe structures having ligaments that bound open cells or closed cells in the interior of the structure.

Figure 2A:
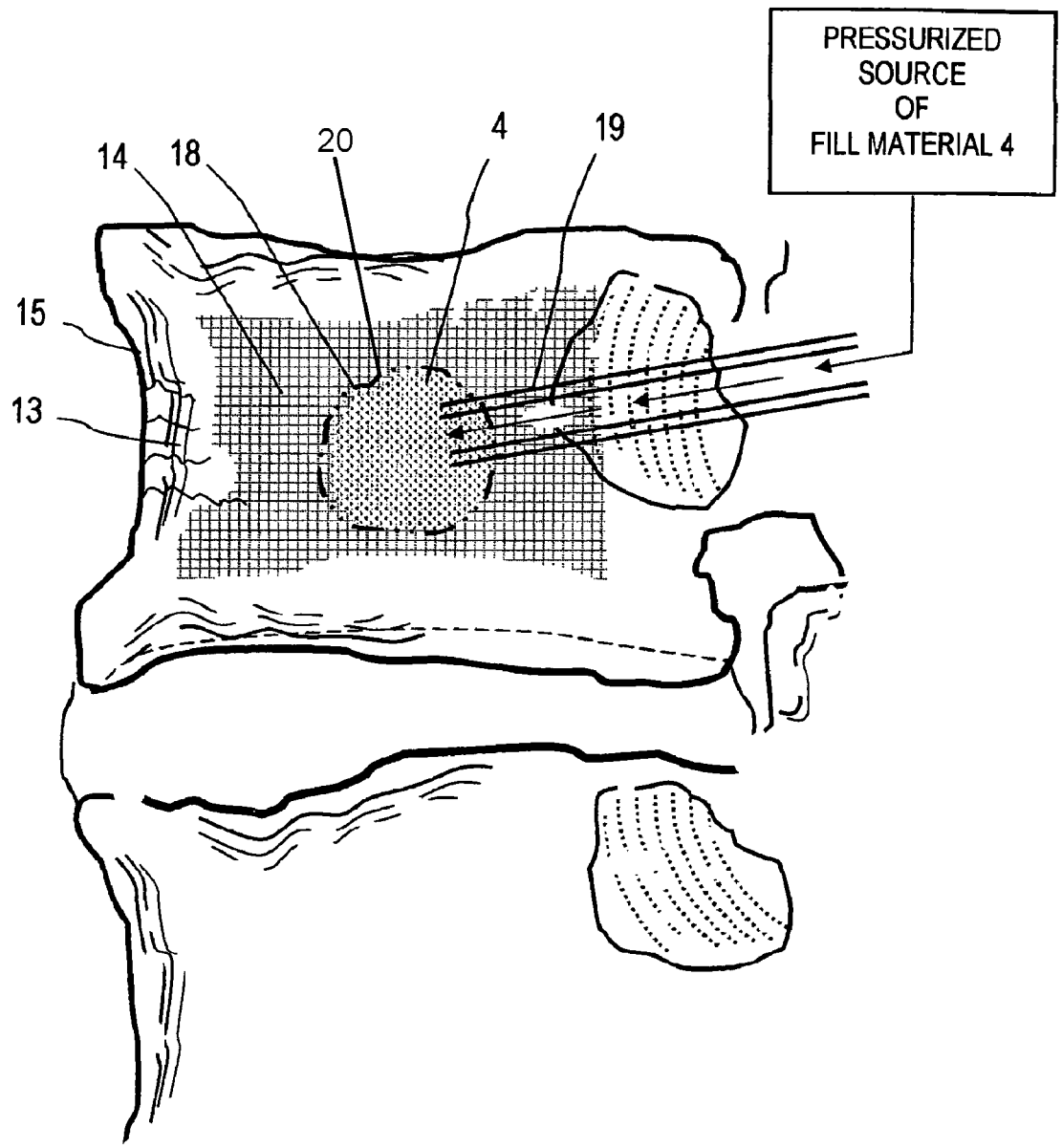
FIG. 2A is a schematic view of a spine segment with a vertebra having a compression fracture showing a method of the invention wherein a volume of the flowable media of FIG. 1A is injected under pressure into cancellous bone in a targeted treatment site.
Figure 2B:
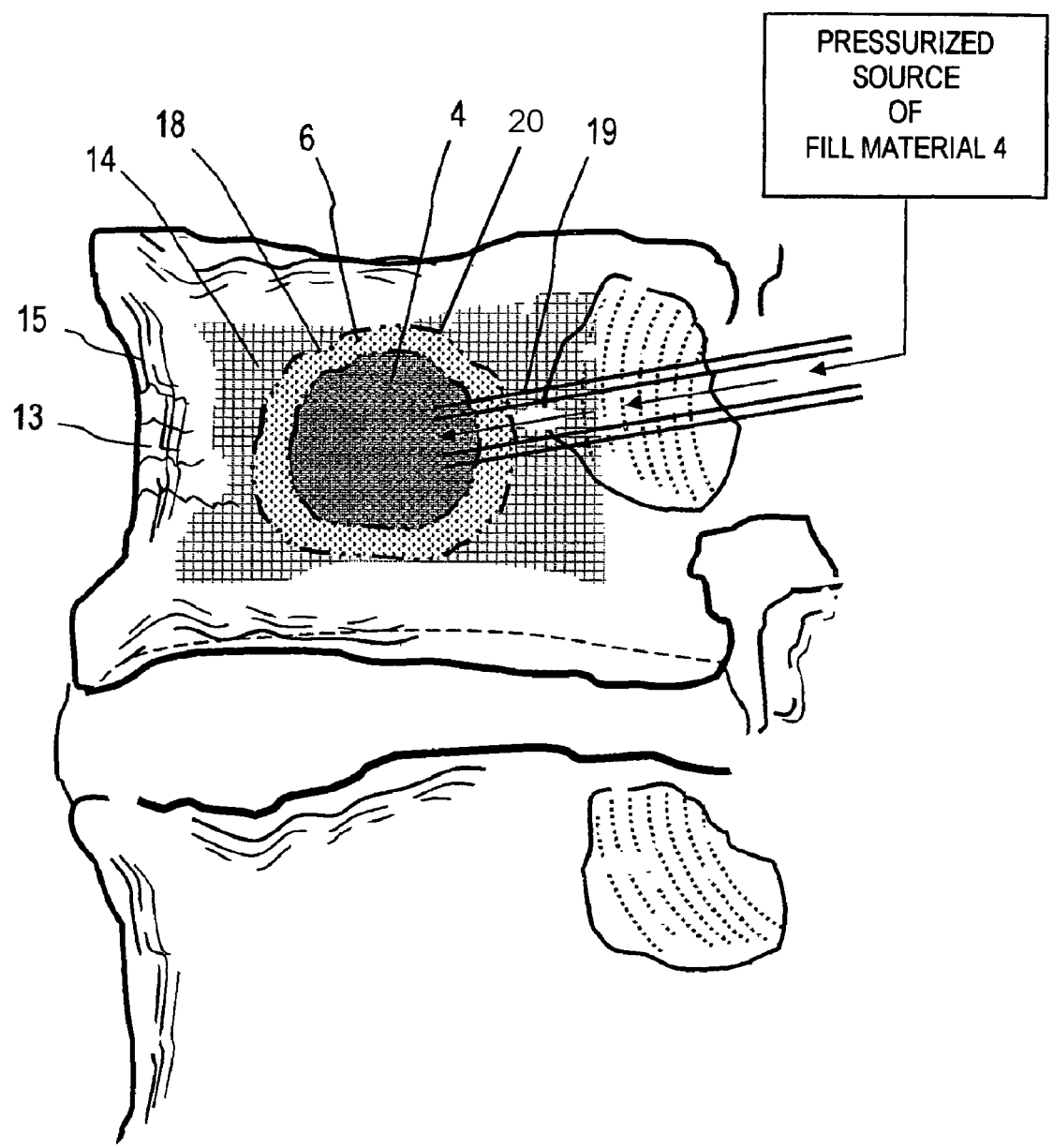
FIG. 2B is a schematic view of the spine segment of FIG. 2A showing the pressurized injection of additional flowable wherein the apparent viscosity of the media is altered at surface regions of the plume by outward migration of the elastomeric element to thereby create flow-impermeable surface regions.

FIG. 2A-2B illustrate a method corresponding to the invention for use in the treatment of a vertebral compression fracture indicated at 13. In FIG. 2A, an initial volume of fill material 4 comprising a flowable bone cement component 5 and intermixed elastomeric elements 6 is injected under substantial pressure into cancellous bone 14 of the vertebra 15 resulting in plume 18. The fill material 4 is introduced in a unilateral or bilateral transpedicular approach through cannula 19 as is well known in the art of vertebroplasty. The fill material 4 propagates within the openings in cancellous bone and may also follow pre-existing fracture lines in cancellous bone, for example as may exist following a compression fracture. FIG. 2B illustrates the same step of injecting fill material 4 but after a greater volume of material has been introduced resulting in plume 18 of fill material being larger and engaging the cortical bone endplates. In the high pressure injection of such a composite fill material, the elastomeric elements 6 migrate toward a surface region 20 of the plume 18 and create a differential in the apparent viscosity of the flowable material across the volume or plume. The term "apparent viscosity" is used herein to describe the flow characteristics of the combination of flowable component 5 and intermixed elastomeric elements 6. As the injection pressures and the resistance to inflows of fill material increase, the accumulation of elastomeric elements 6 about surface region 20 also increases. The elastomeric elements 6 can additionally deform and ultimately the pressures cause elastomeric elements 6 to form in-situ a substantially flow-impermeable surface region 20. As the surface region becomes substantially impermeable to flows or extravasasion therethrough of flowable component 5, continued injection of fill material will elastically expand the surface regions and apply expansion forces to the bone. In a vertebral body as in FIG. 2B, the expansion pressures can expand cancellous bone 14 in which the flowable material 4 has flowed and apply retraction forces to the cortical bone endplates to at least partly reduce a vertebral fracture.

In general, an exemplary method corresponding to the invention for treating mammalian bone comprises the following: (a) flowing an initial volume of flowable media into the interior of a bone wherein the media includes a volume of elastomeric elements, and (b) flowing under pressure increasing volumes of the flowable media wherein injection pressures causes a differential apparent viscosity within selected regions across the flowable media. The method further includes causing surface regions 20 of the plume 18 of flowable media to be substantially impermeable to flows therethrough (FIG. 2B), The method includes allowing an in-situ polymerizable component of the flowable media to harden to thereby support expanded cancellous bone and to maintain retracted cortical bone in an altered position.

In another embodiment, the fill material 4 described above includes an elastomer filler composite 6 that carries microscale or mesoscale reticulated elements 10B (FIG. 1B). As the elastomer elements 6 aggregate about surface region 20 of the plume 18, the reticulated material is proximate to bone and can thus allow for subsequent bone ingrowth. In addition, elastomer elements 6 and surface region 20 create an insulative layer that prevents or moderates heating of the bone external to surface region 20 from an exothermic reaction of a typical bone cement used as flowable component 5 that is interior of surface region 20.

In any embodiment, elastomer composite elements 6 can carry radiosensitive and magnetic-sensitive fillers for cooperating with an RF source or an inductive heating source for elevating the polymer to a targeted temperature. Alternatively, the polymeric composition can be substantially transparent or substantially translucent and carry chromophores for cooperating with a light source introduced with the material for heating the material to a selected temperature for increasing the modulus of the material. Thus, such methods of heating surface regions 20 (FIG. 2B) in which the elastomer composite elements 6 have aggregated will cause accelerated heating of adjacent interior regions of flowable component 5. This system can be used to selectively polymerize regions of flowable media 5 adjacent the surface region 20. By this means, the peripheral portions of plume 18 interior of, and within, the aggregated elastomeric elements, can be formed into a flow-impermeable layer.

The reticulated structures 10B as in FIG. 1B define a mean cross section which can be expressed in microns. In preferred embodiments, the cells are bounded by polyhedral faces, typically pentagonal or hexagonal, that are formed with five or six ligaments 15. The cell dimension is selected for enhancing tissue ingrowth, and mean cell cross-sections can range between 10 microns and 200 microns; and more preferably ranges between 20 microns and 100 microns. Such reticulated materials and structures are available from ERG Materials and Aerospace Corp., 900 Stanford Avenue, Oakland Calif. 94608 and Porvair Advanced Materials, Inc., 700 Shepherd Street, Hendersonville N.C. 28792, and are more fully described in U.S. patent application Ser. No. 11/146,891, filed Jun. 7, 2005 titled Implants and Methods for Treating Bone, the contents of which are incorporated herein by this reference in their entirety and should be considered a part of this specification.

Referring back to FIGS. 1A and 1B, the elastomeric composition comprises any biocompatible polymer having an elastic modulus ranging between about 10 MPa and 1 KPa. The polymer can be a foam, or a shape memory polymer (SMP) that releases stored energy after heating and moving from a compacted temporary shape to an expanded memory shape. A description of suitable shape memory polymers is described in U.S. patent application Ser. No. 10/837,858 titled Orthopedic Implants, Methods of Use and Methods of Fabrication filed May 3, 2004, the contents of which are incorporated herein by this reference in their entirety and should be considered a part of this specification. In a preferred embodiment, the elastomer elements 5 are at least one of bioerodible, bioabsorbable or bioexcretable.

Figure 3A:
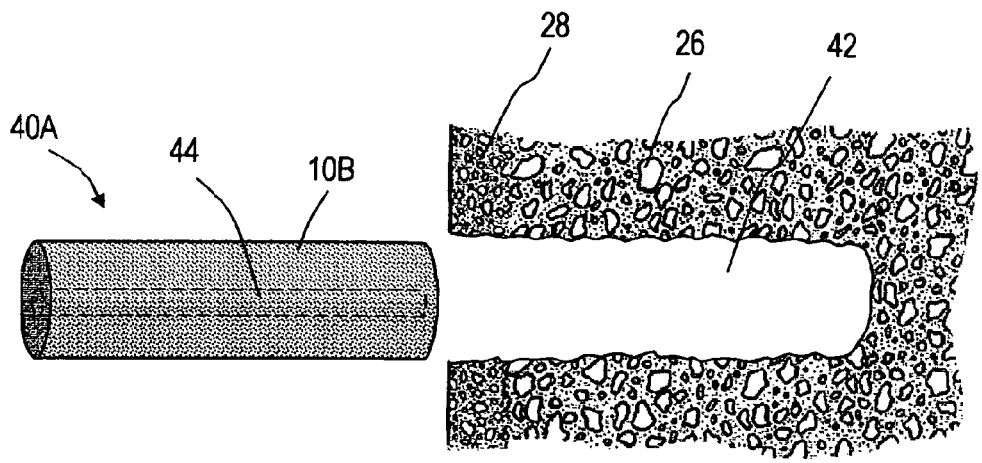
FIGS. 3A-3B are schematic sectional views of a monolith implant structure fabricated of the composite elastomeric material of FIG. 1B; with FIG. 3A illustrating the implant structure introduced into a bore in a bone.
Figure 3B:
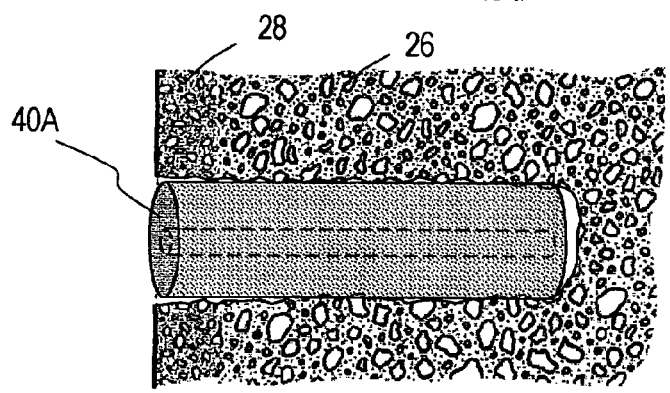
Figure 3C:
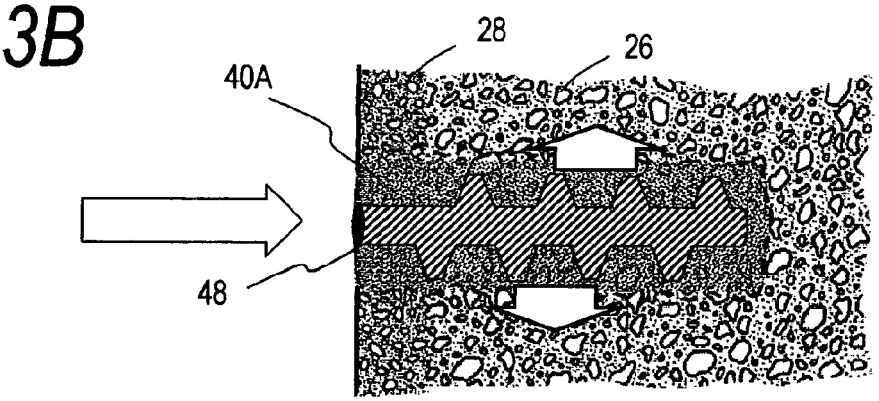
FIG. 3C illustrates an interference fit bone screw driven into the elastomeric material of FIGS. 3A-3B which distributes loads about the bore in cancellous bone.

FIGS. 3A-3C illustrate an alternative embodiment of the invention wherein the composite of an elastomer 10A and reticulated elements 10B (FIG. 1B) is formed into exemplary implant body 40A. In FIGS. 3A and 3B, implant 40A is fabricated by molding in a suitable dimension for introduction into bore 42 in a bone, indicated as cancellous bone 26 and a cortical bone surface 28. FIG. 3C illustrates that implant 40A can have an optional channel or opening 44 for receiving or guiding the positioning of fill material 48 comprising a threaded implant. In FIG. 3C, it can be seen that a threaded implant 48 can be screwed into the implant wherein the elastomeric implant 40A and reticulated elements 10B dispersed therein are compressed to form an interference fit between the bone and implant member 40A. Of particular interest, the insertion of the threaded implant 48 causes self-adjustment of the distribution, location and orientation of the reticulated elements 10B within the elastomer matrix, thus optimally self-distributing loads between the implant 48 and the bone. In the prior art, a threaded implant would engage the bone highest engagement pressures generally about the apex of the threads. In the system as in FIG. 3C, the engagement forces would be distributed about all surfaces of threaded implant 48—which also preferably has a surface region that is reticulated, roughened or porous.

Figure 4:
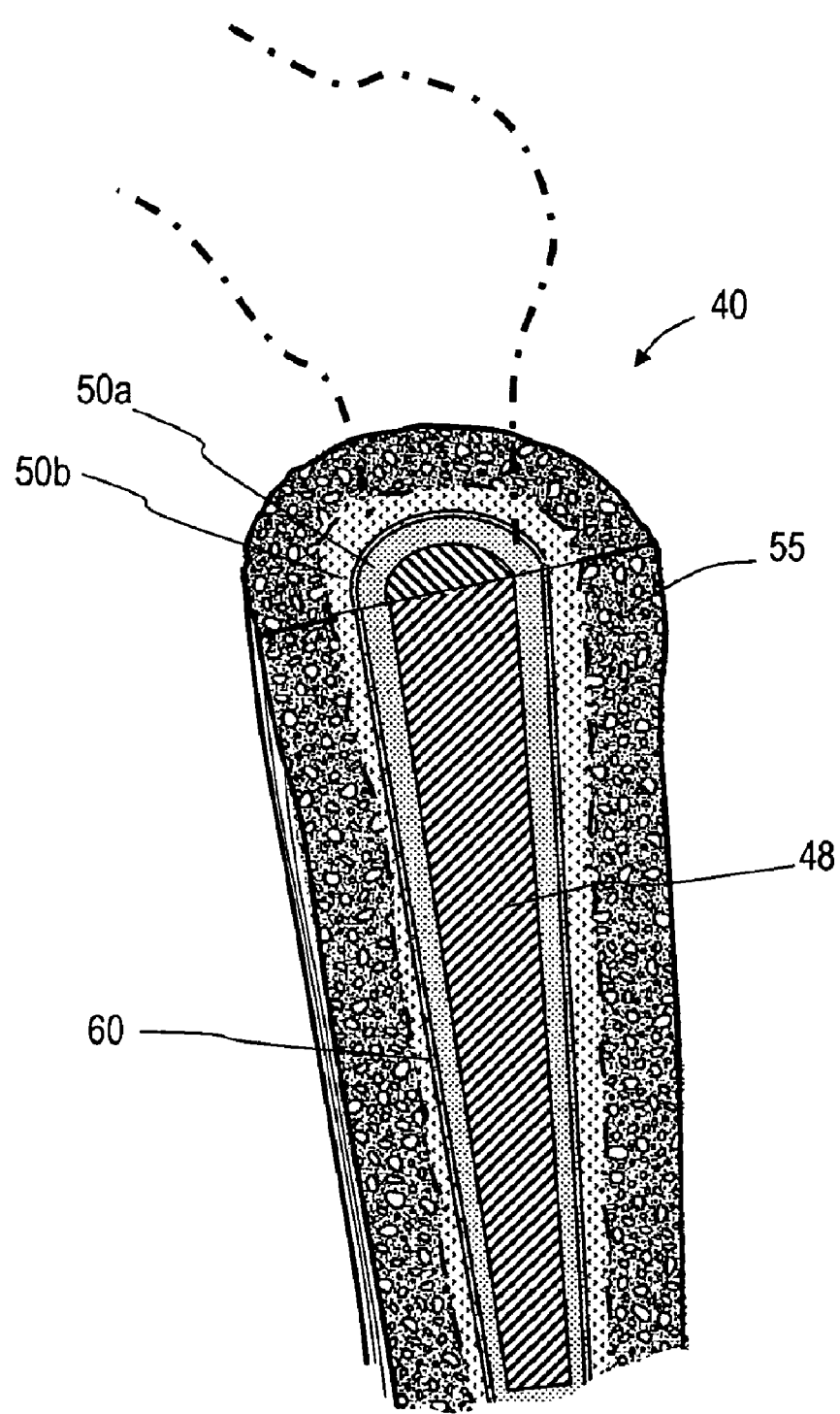
FIG. 4 is a sectional cut-away view of one an implant segment with multiple layers having different moduli.

FIG. 4 illustrates another exemplary implant 40 that is fabricated of an elastomer composite. In this embodiment, the composite body has at least two layers 50a and 50b that are polymer matrices that carry reticulated elements having different parameters (density, cell dimensions etc.) to provide different elastic moduli. The scope of the invention thus encompasses an implant structure 40 that has a gradient modulus for transitioning from an interface with cortical bone 55 to the interface with a rigid member 48 which is needed in various implants and reconstructions, such as in hip implants.

Figure 5A:
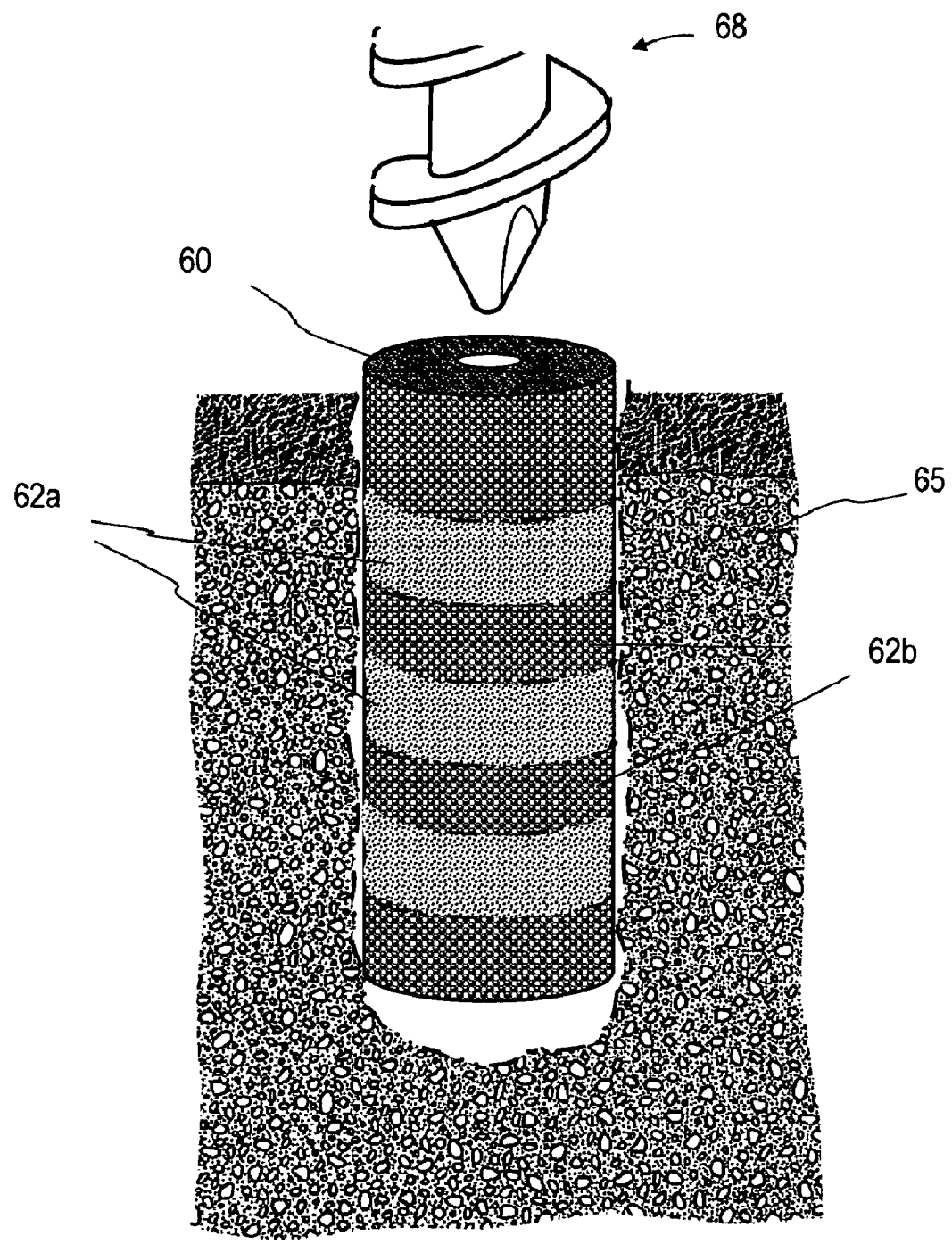
FIGS. 5A-5B show an elastomeric implant with a plurality of composite regions.
Figure 5B:
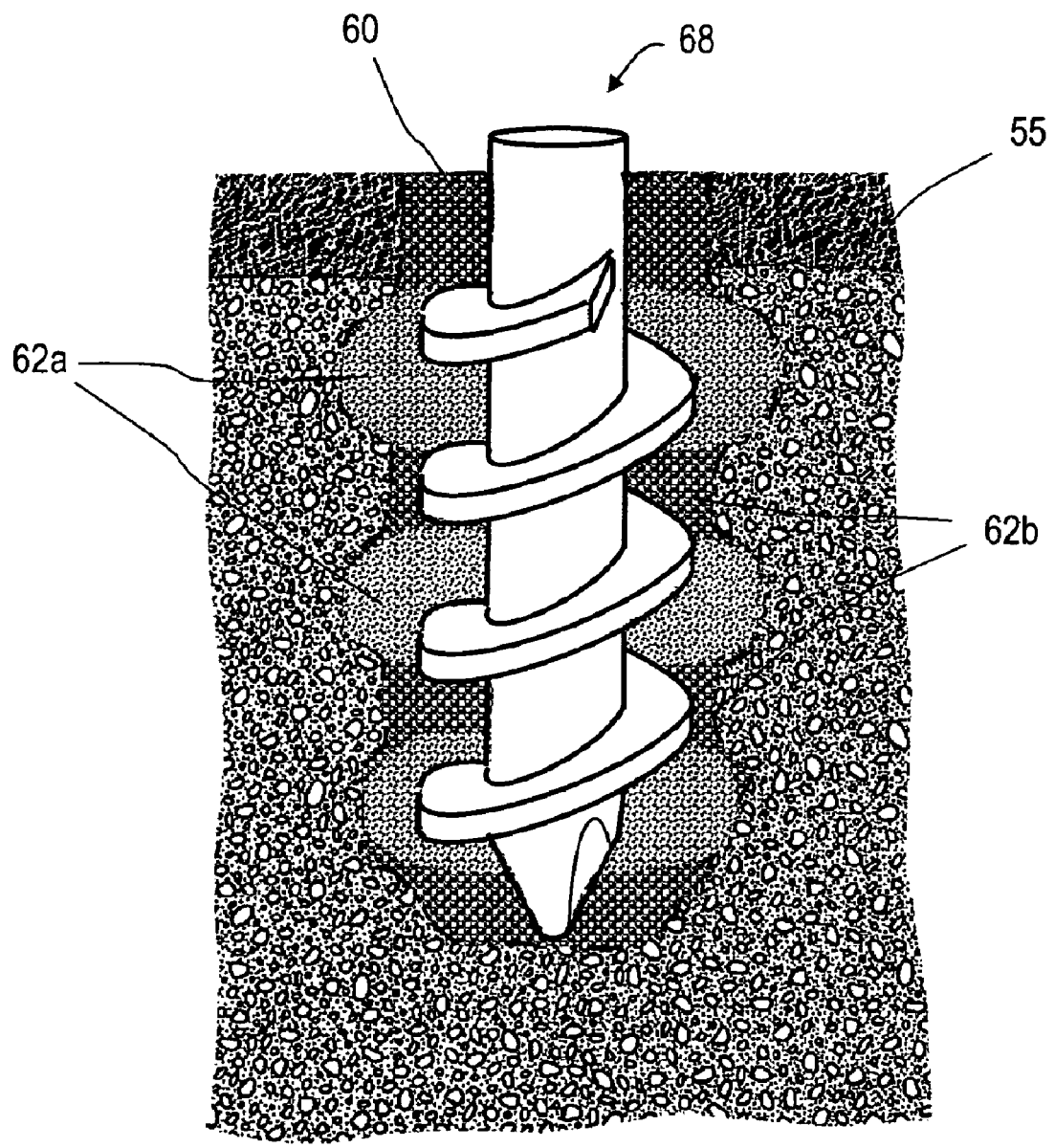

In another embodiment depicted in FIGS. 5A and 5B, the elastomeric composite implant 60 can be configured with a plurality of composite regions 62a and 62b that provide variations or gradients in material properties for enhancing implant fixation in bone 65. In FIG. 5B, it can be seen that regions 62a of the composite are deformable but more rigid than the adjacent regions 62b. Thus, the higher modulus regions will be forced outward more into the bone than other regions 62b upon insertion of bone screw 68. The scope of the invention encompasses varying all the obvious properties of different regions of the composite to achieve the desired regional variations or gradients, and include adjusting the: (i) density of ligaments of the reticulated elements dispersed in the matrix; (ii) the overall shape, dimensions and orientations of the reticulated elements; (iii) the pore size of the reticulated elements; (iv) the modulus, deformability and material of the reticulated elements; (v) the percentage volume of reticulated elements in the matrix, (vi) the properties of media carried in the pores of the reticulated elements, and (vii) the modulus and other properties of the polymer base material 10A (FIG. 1B).

The above-described embodiments describe elastomer composites that cooperate with fill materials to control properties of the interface between fill material and bone. The scope of the invention extends to elastomer composites as in FIGS. 2A-2B, 3A-3C and 4 that are introduced into bone wherein a base polymer can be elevated to a transition temperature so that the composite then adjusts its orientation. Upon cooling, the elastomer composite can then freeze in a particular form. In such embodiments, it is preferred that reticulated elements in the composite have varied shapes for non-slip engagement between such elements to thereby increase the modulus of the material. In an exemplary embodiment, the polymeric composition has a transition temperature in the range of 40° C. to 120° C.; and preferably in the range of 40° C. to 80° C. The transition temperature is a glass transition temperature or a melt temperature. Again, the polymeric matrix can carry radiosensitive or magnetic-sensitive fillers for cooperating with an RF source or an inductive heating source for elevating the polymer to a targeted temperature. Alternatively, the polymeric composition can be substantially transparent or substantially translucent and carry chromophores for cooperating with a light source for heating to material to a selected temperature for elevating the composition to a transition temperature.

In any embodiment, the fill materials or implants can further carry a radiopaque or radiovisible composition if the material of the reticulated elements is not radiovisible.

In any embodiment, the fill materials or implants can carry any pharmacological agent or any of the following: antibiotics, cortical bone material, synthetic cortical replacement material, demineralized bone material, autograft and allograft materials. The implant body also can include drugs and agents for inducing bone growth, such as bone morphogenic protein (BMP). The implants can carry the pharmacological agents for immediate or timed release.

The above description of the invention is intended to be illustrative and not exhaustive. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of treating a bone with an implant comprising:
inserting an elastomeric composite implant body having a predetermined shape into an opening in a bone, the composite implant body defining an internal bore along a longitudinal axis of the composite implant body and comprising:
at least one first region and at least one second region, each region comprising:
an elastomeric polymer; and
reticulated elements dispersed within the elastomeric polymer;
wherein the at least one first region has a different elastic modulus from the at least one second region, the difference being a function of differences between the reticulated elements in the at least one first region as compared to the reticulated elements in the at least one second region;
inserting a rigid insert into the bore in the elastomeric composite implant body to secure the implant in the bone; and
deforming the elastomeric composite implant body with the rigid insert to thereby form an interference fit between the bone and the implant, the at least one first region deforming in a manner different from the at least one second region.

2. The method of claim 1, wherein the at least one first region comprises a plurality of first regions and the at least one second region comprises a plurality of second regions, respective first and second regions alternating sequentially in position as measured axially along the longitudinal axis of the composite implant body and the first regions of the composite implant body are deformable but more rigid than adjacent second regions.

3. The method of claim 2, wherein deforming further comprises forcing the higher modulus first regions farther into the bone than the second regions.

4. The method of claim 1, wherein inserting a rigid insert further comprises advancing a shaft of a hip implant into the bore.

5. The method of claim 1, wherein inserting a rigid insert further comprises inserting a threaded implant into the bore.

6. The method of claim 5, wherein inserting the threaded implant further comprises causing self-adjustment of the distribution, location and orientation of the reticulated elements in both the at least one first region and the at least one second region to self-distribute loads between the implant and the bone.

7. The method of claim 6, wherein inserting the threaded implant further comprises causing the engagement forces between the implant and the bone to be distributed about all surfaces of the threaded implant.

8. The method of claim 5, wherein a surface region of the threaded implant is reticulated, roughened or porous.

9. The method of claim 5, wherein the threaded implant comprises a bone screw.

10. The method of claim 1, wherein the at least one first region is adjacent the at least one second region as measured radially outward from the longitudinal axis of the composite implant body.

11. The method of claim 1, wherein the difference in elastic modulus between the at least one first region and the at least one second region as a function of differences between the reticulated elements comprises at least one of a difference in density; cell dimensions; density of ligaments of the reticulated elements dispersed in the elastomeric polymer; the overall shape, dimensions and/or orientations of the reticulated elements; the pore size of the reticulated elements; the modulus, deformability and/or material of the reticulated elements; the percentage volume of reticulated elements in the elastomeric polymer; and the properties of media carried in pores of the reticulated elements.

12. The method of claim 1, wherein the implant body has a gradient modulus for transitioning from an interface with bone to an interface with the rigid insert.

* * * * *

UNITED STATES PATENT AND TRADEMARK OFFICE
CERTIFICATE OF CORRECTION

PATENT NO.           : 8,163,031 B2
APPLICATION NO.   : 12/942936
DATED                   : April 24, 2012
INVENTOR(S)         : Csaba Truckai et al.

Page 1 of 1

It is certified that error appears in the above-identified patent and that said Letters Patent is hereby corrected as shown below:

At column 1, line 35, delete "billion:" and insert --billion.--, therefor.

At column 2, line 51, delete "pedicles," and insert --pedicles.--, therefor.

At column 3, line 21, delete "Kirby." and insert --Kirby,--, therefor.

At column 3, lines 22-23, delete "polymethlmethacrylate" and insert --polymethylmethacrylate--, therefor.

At column 3, line 28, delete "agent" and insert --agents--, therefor.

At column 4, line 10, after "therein." delete "to".

At column 6, line 4, delete "2B)," and insert --2B).--, therefor.

At column 10, line 2, in claim 10, after "is adjacent" insert --to--.

Signed and Sealed this
Fourth Day of September, 2012

David J. Kappos
*Director of the United States Patent and Trademark Office*